United States Patent
Kawato et al.

(10) Patent No.: US 6,497,860 B1
(45) Date of Patent: Dec. 24, 2002

(54) SKIN LIGHTENING COMPOSITIONS

(75) Inventors: Junji Kawato, Shiga (JP); Ananthanarayan Venkateswaran, Kobe (JP)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 09/297,654

(22) PCT Filed: Nov. 4, 1996

(86) PCT No.: PCT/US96/17522

§ 371 (c)(1),
(2), (4) Date: May 4, 1999

(87) PCT Pub. No.: WO98/19665

PCT Pub. Date: May 14, 1998

(51) Int. Cl.$^7$ .............................. A61K 6/00; A61K 7/00; A61K 7/135

(52) U.S. Cl. ........................................ 424/62; 424/401

(58) Field of Search ..................................... 424/401, 62

(56) References Cited

U.S. PATENT DOCUMENTS

| | | | | |
|---|---|---|---|---|
| 4,136,166 A | * | 1/1979 | Barnett et al. | |
| 4,792,443 A | | 12/1988 | Filomeno | 424/62 |
| 5,514,437 A | | 5/1996 | Tanner et al. | 424/63 |

FOREIGN PATENT DOCUMENTS

| | | | |
|---|---|---|---|
| EP | 419 901 A1 * | 4/1991 | |
| JP | 54129-134 | 3/1978 | |
| JP | 59-157009 | 9/1984 | A61K/7/00 |
| JP | 63-174910 | 7/1988 | |
| JP | 03-101609 | 9/1989 | |
| JP | 3279-313 A | 3/1990 | |
| JP | 04352708 A | 4/1991 | |
| JP | 05139928 A | 4/1991 | |
| JP | 05179300 A | 1/1992 | |
| JP | 6-263624 | 3/1993 | |
| JP | 07025742 A | 7/1993 | |
| JP | 07215888 A | 1/1994 | |
| JP | 08012548 A | 6/1994 | |
| JP | 08012549 A | 6/1994 | |
| JP | 08012550 A | 6/1994 | |
| JP | 08012552 A | 6/1994 | |
| JP | 08012554 A | 6/1994 | |
| JP | 08012556 A | 6/1994 | |
| JP | 08012557 A | 6/1994 | |
| JP | 08012558 A | 6/1994 | |
| JP | 08012565 A | 6/1994 | |
| WO | WO 95/23780 | * 9/1995 | |

* cited by examiner

Primary Examiner—Thurman K. Page
Assistant Examiner—A. Pullian
(74) Attorney, Agent, or Firm—Loy M. White; Steven J. Goldstein

(57) ABSTRACT

Disclosed is a skin lightening composition comprising a) a safe and effective amount of at least one water soluble reducing agent selected from the group consisting of sodium sulfite, potassium sulfite, sodium hydrogen sulfite, potassium, hydrogen sulfite, sodium, metasulfite, potassium metasulfite, ammonium sulfite, ammonium hydrogen sulfite, formic acid, oxalic acid and mixtures thereof and b) cosmetically acceptable carrier for the water soluble reducing agent wherein the composition is substantially free of hydroquinone or its derivatives. Also disclosed is a method for skin lightening in mammals comprising topically applying to the skin the above composition.

17 Claims, No Drawings

SKIN LIGHTENING COMPOSITIONS

TECHNICAL FIELD

The present invention relates to the field of skin lightening. Specifically, the present invention relates to novel compositions comprising a specific reducing agent for skin lightening.

BACKGROUND

The formation of melanin depends upon the availability of three substances: (1) a suitable substrate such as tyrosine and dopa, (2) molecular oxygen and (3) enzyme tyrosinase (a copper protein complex). If any of these substances are absent or reduced, the formation of melanin is impaired.

The reducing agent retards melanin formation by the following three mechanism: (1) It sequesters some of the copper in the enzyme system and the enzymatic formation of melanin is reduced by sequestering copper since the co-enzyme of tyrosinase is a copper protein complex. (2) The necessary substrates for melanin formation(tyrosine and dopa) are formed from both bacteriological and enzymatic breakdown of protein. A decrease in the available bacteria would depress proteolytic destruction and thereby aid in decreasing melanogensis since the reducing agent such as sodium sulfite is a bactericide. (3) The strong reducing agent such as sodium sulfite itself gets oxidized in preference to the melanin substrates..

Romanian patent application No. 100161 is assigned to Institute of Chemical-Pharmaceutical Research, Bucharest and discloses that a reducing agent such as sodium metabisulfite is used to eliminate the unpleasant odor.

U.S. Pat. No. 4,13,6166 is assigned to Helena Rubinstein, U.S. Pat. No. 4,792,443 is assigned to Warner-Lambert, U.S. Pat. No. 5,514,437 is assigned to The Proctor & Gamble Company and Japanese Patent Laid-open No.6-263624 is assigned to Mochida Pharmaceutical Co. and they disclose that sulfite salts, hydrogen sulfite salts and metabisulfite salts are used as a stabilizer or an antioxidant.

Japanese Patent Laid-open No.54-129134 is assigned to Shiseido and discloses that a combination of (i) sulfite or hydrogensulfite and organic solvent, (ii) ferrous salt and (iii) hydrogen peroxide shows an effect of bleaching a melanin of hair.

Japanese Patent Laid-open No. 3-101609 is assigned to Sansyo Pharmaceutical, No.3-279313 is assigned to Shiseido, No. 4-352708 is assigned toKose, No. 63-174910 is assigned to Shiseido and No. 7-25742 is assigned to Kao, and they disclose that sulfites, hydrogensulfites and pyrosulfites have an effect of preventing the product from coloring.

Japanese Patent Laid-open No. 5-139928 is assigned to Hisamitsu Pharmaceutical Co. and discloses that sodium hydrogen sulfite and sodium metabisulfite are used as an antioxidant.

Japanese Patent Laid-open No. 5-179300 is assigned to Kitano Kagaku and discloses that sodium hydrogen sulfite is used to bleach leather.

Japanese Patent Laid-open Nos. 7-215888, 8-12548, 8-12549, 8-12550, 8-12552, 8-12554, 8-12556, 8-12557, 8-12558 and 8-12565 are assigned to Shiseido and Japanese Patent Laid-open No. 59-157009 is assigned to Yakurigaku Cyuo kenkyusho and they disclose that very low level of sodium hydrogensulfite or sodium sulfite is included in a skin lightening or melanin controlling composition comprising a specific skin lightening or melanin controlling active ingredient.

It has been discovered that the water-soluble reducing agent selected from the group consisting of sodium sulfite, potassium sulfite, ammonium sulfite, sodium hydrogen sulfite, potassium hydrogen sulfite, ammonium hydrogen sulfite, sodium metabisulfite, potassium metabisulfite, formic acid and oxalic acid, and mixtures thereof lightens mammalian skin.

SUMMARY

The present invention relates to skin lightening cosmetic compositions comprising:
a) a safe and effective amount of at least one water-soluble reducing agent selected from the group consisting of sodium sulfite, potassium sulfite, ammonium sulfite, sodium hydrogen sulfite, potassium hydrogen sulfite, ammonium hydrogen sulfite, sodium metabisulfite, potassium metabisulfite, formic acid, oxalic acid, and mixtures thereof
b) a cosmetically acceptable carrier for the water-soluble reducing agent wherein said compositions are substantially free of hydroquinone or its derivatives.

The skin lightening compositions of the present invention preferably comprise said water-soluble reducing agent and lecithin.

The skin lightening compositions of the present invention more preferably comprise (a) said water-soluble reducing agent, (b) a cosmetically acceptable liquid oil, (c) a polyhydric alcohol, (d) a solid fatty alcohol, (e) surfactant, (f) water and (g) lecithin, wherein at least a portion of the above components (a), (b), (c), (d), (e), (f) and (g) forms a liquid crystal.

Such compositions satisfy the need for skin lightening effect of mammalian skin

DETAILED DESCRIPTION

As used herein, "topical application" means directly laying on or spreading on outer skin.

As used herein, "skin lightening" means decreasing melanin in skin, including one or more of overall lightening of basal skin tone, lightening of hyperpigmented lesions including age spots, melasma, chloasma, freckles, post inflammatory hyperpigmentation or sun-induced pigmented blemishes.

As used herein, "solid" means solid form at the temperature of 25° C., and "liquid" means liquid form at the temperature of 25° C.

As used herein, all percentages are by weight unless otherwise specified.

A. Water-soluble Reducing Agent

The composition of the present invention comprises a water-soluble reducing agent. The reducing agent is selected from the group consisting of sodium sulfite, potassium sulfite, ammonium sulfite, sodium hydrogen sulfite, potassium hydrogen sulfite, ammonium hydrogen sulfite, sodium metabisulfite, potassium metabisulfite, formic acid, oxalic acid, and mixtures thereof. If the composition comprises more than about 5% by weight of the composition, of the reducing agent, it will cause safety issue, and if it comprises less than 0.1% by weight of the composition, of the reducing agent, enough skin lightening effect is not expected.

The skin lightening composition of the present invention comprises preferably from about 0.1% to about 5%, more preferably from about 0.15% to about 5%, still more preferably from about 0.2% to about 5%, most preferably from about 0.25% to about 5% by weight of the composition, of the reducing agent.

In the reducing agent, sodium sulfite, sodium hydrogen sulfite, sodium metabisulfite and the mixtures thereof are preferred.

The skin lightening composition of the present invention is substantially free of hydroquinone or its derivatives, and preferably hydroquinone and its derivatives are absent from the present invention as they are thought to disturb the lightening activity of the water-soluble reducing agent. Such hydroquinone derivatives include 4-[(tetrahydro-2H-pyran-2-yl)oxy]phenol and 4-[(tetrahydro-2H-thiopyran-2-yl)oxy]phenol and ones which are described in WO 9523780 which is hereby incorporated by reference.

B. Lecithin

The skin lightening composition of the present invention preferably comprises said water-soluble reducing agent and lecithin. Lecithin is a natural product derived from soybean or egg yolk, and used for enhancing the skin lightening effect of the reducing agent. If the composition comprises more than 10% by weight of the composition, of lecithin, it will cause tackiness problem, and if it comprises less than 0.01% by weight of the composition, of lecithin, enough enhancing effect of the skin lightning effect of the reducing agent is not expected.

The lecithin level in the skin lightening composition of the present invention is preferably from about 0.01% to about 10%, more preferably from about 0.5% to about 3% by weight of the composition.

C. Cosmetically Acceptable Carrier

The phrase "cosmetically acceptable carrier", as used herein, means one or more compatible solid or liquid fillers, diluents, extenders and the like, which are cosmetically acceptable as defined herein. The term "compatible", as used herein, means that the components of the compositions of this invention are capable of being comingled with the primary actives of the present invention, and with each other, in a manner such that there is no interaction which would substantially reduce the efficacy of the composition under ordinary use situations. The type of carrier utilized in the present invention depends on the type of product desired. The topical compositions useful in the present invention may be made into a wide variety of product types. These include, but are not limited to, lotions, creams, gels, sticks, sprays, ointments, pastes, mousses and cosmetics (e.g., solid, semi-solid, liquid make-up, including foundations). These product types may comprise several types of carriers including, but not limited to solutions, aerosols, emulsions (including water-in-oil and oil-in-water), gels, solids, and liposomes.

Solutions according to the present invention typically include water and cosmetically acceptable organic solvent. Water is a preferred solvent. Examples of suitable organic solvents include: propylene glycol, polyethylene glycol (e.g., Molecular Weight 200–600 g/mole), polypropylene glycol (e.g., Molecular Weight 425–2025 g/mole), glycerol, 1,2,4-butanetriol, 1,2,6-hexanetriol, ethanol, isopropanol, sorbitol esters, butanediol, and mixtures thereof. Solutions useful in the present invention preferably contain from about 50% to about 99.9% of water or both water and an acceptable organic solvent, and the water-soluble reducing agent in the above described amounts.

Aerosols according to the present invention can be formed by adding a propellant to a solution such as described above. Exemplary propellants include chloro-fluorinated lower molecular weight hydrocarbons. Additional propellants that are useful herein are described in Sagarin, *Cosmetics Science and Technology,* 2nd Edition, Vol. 2, pp. 443–465 (1972), incorporated herein by reference. Aerosols are typically applied to the skin as a spray-on product.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and *McCutcheon's Detergents and Emulsifiers,* North American Edition, pages 317–324 (1986), each incorporated herein by reference.

The emulsion may also contain an anti-foaming agent to minimize foaming upon application to the skin. Anti-foaming agents include high molecular weight silicones and other materials well known in the art for such use.

The emulsions preferably comprise a silicone for imparting a preferred skin feel. Generally such silicones have a low molecular weight. Suitable silicones include cyclomethicones, dimethicones,and blends having cyclomethicones, dimethicones and/or dimethiconol, such as Dow Corning 200 fluid (especially 10 cs) and Dow Corning Q2-1401. Such silicones are commercially available from the Dow Corning Corp. of Midland, Mich.

The topical compositions of the present invention may comprise a topical cosmetically acceptable emollient. Such compositions preferably contain from about 2% to about 50% of the emollient. As used herein, "emollient" refers to a material used for the prevention or relief of dryness, as well as for the protection of the skin. A wide variety of suitable emollients are known and may be used herein. Sagarin, *Cosmetics, Science and Technology,* 2nd Edition, Vol. 1, pp. 32–43 (1972), incorporated herein by reference, contains numerous examples of materials suitable as an emollient.

Lotions and creams according to the present invention generally comprise a solution carrier system and one or more emollients. Lotions typically comprise from about 0.01% to about 50%, preferably from about 0.1% to about 20%, of emollient; from about 30% to about 99%, preferably from about 50% to about 90% of water; and the primary actives in the above described amounts. A cream typically comprises from about 5% to about 50%, preferably from about 10% to about 30%, of emollient; from about 45% to about 90%, preferably from about 50% to about 85% of water; and the primary actives in the above described amounts.

D. Formation of a Liquid Crystal

The skin lightening composition of the present invention more preferably comprises (a) said water-soluble reducing agent, (b) a cosmetically acceptable liquid oil, (c) a polyhydric alcohol, (d) a solid fatty alcohol, (e) surfactant, (f) water and (g) lecithin, wherein at least a portion of the above components (a), (b), (c), (d), (e), (f) and (g) forms a liquid crystal.

The liquid crystal can be detected by observing the shape of the liquid crystal by a polarization microscope.

The level of the cosmetically acceptable liquid oil in the skin lightening composition of the present invention comprising the liquid crystal is preferably from about 1% to about 50%, more preferably from about 3% to about 25% by weight of the composition.

The level of the polyhydric alcohol in the skin lightening composition of the present invention comprising the liquid crystal is preferably from about 0.1% to about 20%, more preferably from about 1% to about 10% by weight of the composition.

The level of the solid fatty alcohol in the skin lightening composition of the present invention comprising the liquid crystal is preferably from about 0.1% to about 20%, more preferably from about 1.0% to about 5% by weight of the composition.

The level of the surfactant in the skin lightening composition of the present invention comprising the liquid crystal is preferably from about 0.1% to about 10%, more preferably from about 0. 1% to about 3% by weight of the composition.

The level of the water in the skin lightening composition of the present invention comprising the liquid crystal should be preferably from about 40% to about 90%, more preferably from about 60% to about 90% by weight of the composition.

The level of the lecithin in the skin lightening composition of the present invention comprising the liquid crystal is preferably from about 0.01% to about 10%, more preferably from about 0. 1% to about 3% by weight of the composition.

The skin lightening composition of the present invention comprising the liquid crystal may be made into an emulsion type product. The emulsion type product includes, but are not limited to, milky lotions and creams.

The examples of a cosmetically acceptable liquid oil, a polyhydric alcohol, a solid fatty alcohol and a surfactant, which can be used to form a liquid crystal, are as follows.

(1)Cosmetically Acceptable Liquid Oil

The cosmetically acceptable liquid oil is included in said cosmetically acceptable carrier. The cosmetically acceptable liquid oil is in liquid form at room temperature. The cosmetically acceptable liquid oil can be liquid hydrocarbon oil, liquid natural oil, liquid fatty alcohol, liquid fatty acid, liquid fatty acid ester, liquid silicone oil, and paste wax and mixtures thereof.

Non-limiting examples of the liquid hydrocarbons are squalane, liquid mineral oil, and liquid polybutene.

Non-limiting examples of the liquid natural oil derived from plants useful in the present invention include almond oil, olive oil, sesami oil, safflower oil, avocado oil, cottonseed oil, jojoba oil, castor oil, soybean oil, palm kernel oil, coconut oil, and hydrogenated vegetable oil. Non-limiting examples of the liquid natural oil derived from animal sources useful in the present invention include mink oil and egg yolk oil.

Non-limiting examples of the liquid fatty alcohol useful in the present invention are isostearyl alcohol, lanolin alcohol, oleyl alcohol, hexadecyl alcohol, octyldodecanol alcohol, linoleyl alcohol, linolenyl alcohol, lauryl alcohol and arachidyl alcohol.

Fatty acid can be natural or synthetic, saturated, unsaturated, linear, or branched. Non-limiting examples of fatty acid useful in the present invention are caprylic, isostearic, linoleic, ricinoleic, and oleic acid.

Non-limiting examples of the liquid fatty acid ester useful in the present invention are cetyl octanoate, glyceryl trioctanoate, isopropyl linoleate, isopropyl myristate, isopropyl oleate, ethyl laurate, ethyl linoleate, octyl dodecyl myristate, octyl palmitate, octyl isopelargonate, octyl dodecyl lactate, isotridecyl isononanoate, oleyl oleate, isostearyl myristate, neopentyl glycol dioctanoate, and di(capryl/capric acid) propylene glycol and mixtures thereof. Other suitable esters include triglycerides such as caprylic triglycerides, capric triglyceride, isostearic triglyceride and adipic triglyceride.

Non-volatile, straight, and branched silicone oil such as dimethicone and phenyl dimethicone is also useful.

Other cosmetically acceptable liquid oil includes octyl methoxy cinnamate, cinoxate, and 2-ethylphexyl p-dimethyaminobenzoate.

Either one kind or two or more kinds of the cosmetically acceptable liquid oil can be used in the present invention.

The cosmetically acceptable liquid oil can also act as an emollient, and can provide adhesion and durability properties to the cosmetic.

(2) Polyhydric Alcohol

Polyhydric alcohol include glycerin, diglycerin, triglycerin, polyglycerin, polypropylene glycol, polyethylene glycol, ethylene glycol, diethylene glycol, triethylene glycol, propylene glycol, dipropylene glycol, hexylene glycol, 1,3-butylene glycol, 1,4-butylene glycol, ethylene glycol monoalkyl ether, diethylene glycol monoalkyl ether, glucose, maltose, sucrose, lactose, xylitose, xylitol, sorbitol, mannitol, maltitol, malbit, panthenol, pentaerythritol, and hyaluronic acid and its salts. Among the polyhydric alcohols, glycerin is preferred.

Either one kind or two or more kinds of the polyhydric alcohol can be used in the present invention.

(3) Solid Fatty Alcohol

Solid fatty alcohols include arachidyl alcohol, cetyl alcohol, stearyl alcohol, behenyl alcohol, myristyl alcohol, batyl alcohol, cholesterol and phytosterol. Among the solid fatty alcohols, cetyl alcohol is preferred.

Either one kind or two or more kinds of the solid fatty alcohol can be used in the present invention.

(4) Surfactant

Surfactants include nonionic surfactant and anionic surfactants.

Nonionic surfactants include alkanolamides such as coconut diethanolamide and lauramide DEA, block polymers such as block copolymer of propylene oxide and ethylene oxide, ethoxy fatty acids such as propyleneglycol monostearate, ethoxylated alcohols such as polyoxyethylene (20) stearyl ether, ethoxylated alkylphenols such as polyoxyethylene (10) nonylphenyl ether, ethoxylated fatty acids such as polyethyleneglycol (10 ethylene oxide) monostearate, ethoxylated fatty esters such as polyoxyethylene (5) glyceryl monostearate, ethoxylated fatty esters and oils such as polyoxyerthylene (10) hydrogenated castor oil and polyoxyethylene (6) sorbitol beeswax, glycerol esters such as glyceryl monostearate and diglyceryl monostearate, lanolin-based derivatives such as polyoxyethylene lanolin, propoxylated and ethoxylated fatty acids, alcohols or alkyl phenols such as polyoxyethylene (10) polyoxypropylene (4) cetyl ether, protein-based surfactants such as polyoxyethylene (25) glycerin monopyoglutamic monoisostearate, solbitan derivatives such as sorbitan monostearate, polyoxyethylene (20) sorbitan monostearate and polyoxyethylene (60) sorbitol tetrastearate and sucrose and glucose esters and derivatives such as saccharose distearate and sucrose stearate.

Anionic surfactants include phosphate ester such as sodium polyoxyethylene (4) lauryl ether phosphate and DEA cetyl phosphate, phosphorous organic derivatives such as phosphated oleyl ether (10 ethylene oxide) and soaps such as sodium stearate and potassium cocoate.

Either one kind or two or more kinds of surfactant can be used in the present invention.

E. Combination Actives
(1) Sunscreens and Sunblocks

Regulation of skin darkening resulting from exposure to ultraviolet light can be achieved by using combinations of the active skin lightening agents together with sunscreens or sunblocks. Useful sunblocks include, for example, zinc oxide and titanium dioxide.

Ultraviolet light is a predominant cause of skin darkening. Thus, for purposes of skin lightening, the combination of the water-soluble reducing agent with a UVA and/or UVB sunscreen is desirable.

A wide variety of conventional sunscreening agents are suitable for use in combination with the skin lightening agent. Segarin, et al., at Chapter VIII, pages 189 et seq., of *Cosmetics Science and Technology,* disclose numerous suitable agents. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); Cinnamic acid derivatives (menthyl and benzyl esters, butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxy-naphthoic acid and its salts; o- and p-Hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); hydroxy- or methoxy-substituted benzophenones; uric and vilouric acids; tannic acid and its derivatives (e.g., hexaethylether); (butyl carbotol) (6-propyl piperonyl) ether; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; and 4-isopropyl-di-benzoylmethane.

Of these, 2-ethylhexyl-p-methoxycinnamate, 4,4'-t-butyl methoxydibenzoyl-methane, 2-hydroxy-4-methoxybenzophenone, octyldimethyl-p-aminobenzoic acid, digalloyltrioleate, 2,2--dihydroxy-4-methoxybenzophenone, ethyl-4(bis(hydroxypropyl)) aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid and mixtures of these compounds, are preferred.

More preferred sunscreens useful in the compositions useful in the present invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are
4-N,N-(2-ethylhexyl)methylaminobenzoic acid ester of 2,4-dihydroxybenzophenone;
N,N-di-(2-ethylhexyl)-4-aminobenzoic acid ester with 4-hydroxydibenzoylmethane;
4-N,N-(2-ethylhexyl) methylaminobenzoic acid ester with 4-hydroxydibenzoylmethane; 4-N,N-(2-ethylhexyl) methylaminobenzoic acid ester of 2-hydroxy4-(2-hydroxy-ethoxy)benzophenone; 4-N,N-(2-ethylhexyl)-methylaminobenzoic acid ester of 4-(2-hydroxyethoxy) dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

A safe and effective amount of sunscreen may be used in the compositions useful in the present invention. The sunscreening agent must be compatible with the water-soluble reducing agent. The composition preferably comprises from about 1% to about 20%, more preferably from about 2% to about 10%, of a sunscreening agent. Exact amounts will vary depending upon the sunscreen chosen and the desired Sun Protection Factor (SPF).

An agent may also be added to any of the compositions useful in the present invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

(2) Anti-Inflammatory Agents

In a preferred skin lightening composition useful in the present invention, an anti-inflammatory agent is included as an active along with the water-soluble reducing agent. The inclusion of an anti-inflammatory agent enhances the skin lightening benefits of the compositions. The anti-inflammatory agent protects strongly in the UVA radiation range (though it also provides some UVB protection as well). The topical use of anti-inflammatory agents reduces darkening of the skin resulting from chronic exposure to UV radiation. (See U.S. Pat. No. 4,847,071, Bissett, Bush, and Chatterjee, issued Jul. 11, 1989, incorporated herein by reference; and U.S. Pat. No. 4,847,069, Bissett and Chatterjee, issued Jul. 11, 1989, incorporated herein by reference.)

A safe and effective amount of an anti-inflammatory agent may be added to the compositions useful in the present invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexanethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentyl-propionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be had to standard texts, including *Antiinflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974).

Specific non-steroidal anti-inflammatory agents useful in the composition invention include, but are not limited to:
  i) the oxicams, such as piroxicam, isoxicam, tenoxicam, sudoxicam, and CP-14,304;
  ii) the salicylates, such as aspirin, disalcid, benorylate, trilisate, safapryn, solprin, diflunisal, and fendosal;
  iii) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac;
  iv) the fenamates, such as mefenamic, meclofenamic, flufenamic, niflumic, and tolfenamic acids;
  v) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and
  vi) the pyrazoles, such as phenybutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Another class of anti-inflammatory agents which are useful in the compositions are the anti-inflammatory agents disclosed in U.S. Pat. No. 4,708,966, Loomans et al., issued Nov. 24, 1987. This patent discloses a class of nonsteroidal anti-inflammatory compounds which comprise specifically substituted phenyl compounds, especially substituted 2,6-di-tert-butyl phenol derivatives. For example, compounds selected from 4-(4'-pentyn-3'one)-2,6-di-t-butylphenol; 4-(5'-hexynoyl)-2,6-di-t-butylphenol; 4-((S)-(−)-3'-methyl-5'-hexynoyl)-2,6-di-t-butylphenol; 4-((R)-(+)-3'-methyl-5'-hexynoyl)-2,6-di-butylphenol; and 4-(3',3'-dimethoxypropionyl)-2,6-di-t-butylphenol are useful in methods of the present invention;

4-(5'-hexynoyl)-2,6-d-t-butylphenol is most preferred.

Yet another class of anti-inflammatory agents which are useful in the compositions are those disclosed in U.S. Pat. No. 4,912,248, Mueller, issued Mar. 27, 1990. This patent discloses compounds and diastereomeric mixtures of specific 2-naphthyl- containing ester compounds, especially naproxen ester and naproxol ester compounds, having two or more chiral centers. For example, compounds selected from (S)-naproxen-(S)-2-butyl ester, (S)-naproxen-(R)-2-butylester, (S)naproxol-(R)-2-methyl butyrate, (S)-naproxol-(S)-2-methyl butyrate, diasteromeric mixtures of (S)-naproxen-(S)-2-butyl ester and (S)-naproxen-(R)-2-butyl ester, and diasteromeric mixtures of (S)-naproxol-(R)-2-methyl butyrate and (S)-naproxol-(S)-2-methyl butyrate are useful in the present invention.

Finally, so-called "natural" anti-inflammatory agents are useful in methods of the present invention. For example, candelilla wax, alpha bisabolol, aloe vera, Manjistha (extracted from plants in the genus Rubia particularly *Rubia Cordifolia*, and Guggal (extracted from plants in the genus Commiphora, particularly *Commiphora Mukul*), may be used.

Another preferred composition useful in the present invention comprises a skin lightening agent, a sunscreen, and an anti-inflammatory agent together for skin lightening in the amounts disclosed for each individually hereinabove.

(3) Anti-Oxidants/Radical Scavengers

In a preferred skin lightening composition useful in the present invention, an anti-oxidant/radical scavenger is included as an active along with the skin lightening agent. The inclusion of an anti-oxidant/radical scavenger increases the skin lightening benefits of the composition.

A safe and effective amount of an anti-oxidant/radical scavenger may be added to the compositions useful in the present invention, preferably from about 0.1% to about 10%, more preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox,), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxy fumaric acid and its salts may be used.

In a preferred composition useful in the present invention, compositions comprise one, any two, or all three of a sunscreening agent, anti-inflammatory agent, and/or an anti-oxidant/radical scavenging agent included as actives along with the skin lightening agent. The inclusion of two or all three of these agents with the skin lightening agent increases the skin lightening benefits of the composition.

(4) Chelators

In a preferred composition useful in the present invention, a chelating agent is included as an active along with the skin lightening agent. As used herein, "chelating agent" means an active agent capable of removing a metal ion from a system by forming a complex so that the metal ion cannot readily participate in or catalyze chemical reactions. The inclusion of a chelating agent increases the skin lightening benefits of the composition.

A safe and effective amount of a chelating agent may be added to the compositions useful in the present invention, preferably from about 0.1% to about 10%, more preferably from about 1% to about 5%, of the composition. Chelators useful in compositions are disclosed in U.S. patent application Ser. No. 619,805, Bissett, Bush & Chatterjee, filed Nov. 27, 1990 (which is a continuation of U.S. patent application Ser. No. 251,910, filed Oct. 4, 1988); U.S. patent application Ser. No. 514,892, Bush & Bissett, filed Apr. 26, 1990; and U.S. patent application Ser. No. 657,847, Bush, Bissett & Chatterjee, filed Feb. 25, 1991; all incorporated herein by reference. Preferred chelators useful in compositions of the present invention are furildioxime and derivatives thereof.

In a preferred composition useful in the present invention, compositions comprise one, any two, any three, or all four of a sunscreening agent, anti-inflammatory agent, anti-oxidant/radical scavenging agent, and/or chelating agent included as actives along with the skin lightening agent. The inclusion of two, three, or all four of these agents with the skin lightening agent increases the skin lightening benefits of the composition.

(5) Retinoids

In a preferred composition useful in the present invention, a retinoid, preferably retinoic acid, is included as an active along with the skin lightening agent. The inclusion of a retinoid increases the skin lightening benefits of the composition. A safe and effective amount of a retinoid may be added to the compositions useful in the present invention, preferably from about 0.001% to about 2%, more preferably from about 0.01% to about 1% of the composition. As used herein, "retinoid" includes all natural and/or synthetic analogs of Vitamin A or retinol-like compounds which possess the biological activity of Vitamin A in the skin as well as the geometric isomers and stereo isomers of these compounds, such as all-trans retinoic acid and 13-cis-retinoic acid.

In a preferred composition useful in the present invention, compositions comprise one, any two, any three, any four, and/or all five of a sunscreening agent, anti-inflammatory agent, anti-oxidant/radical scavenging agent, chelating agent, and/or a retinoid included as actives along with the skin lightening agent. The inclusion of two, three, four, or all five of these agents with the skin lightening agent increases the skin lightening benefits of the composition.

(6) Other Optional Components

Other optional components include thickeners such as carboxy vinyl polymer, preservatives, liquid and paste pigments, astringents, pH buffers, perfumes, infrared screening agents, amphoteric and solid amorphous lipids, vitamins, nutrients, and skin conditioning agents.

Useful skin conditioning agents are beta-glycyrrhetic acid and its derivatives, vegetation extracts, alantoin, collagen, and extract and treated elastin fibers.

F. Methods for Lightening Skin in Mammals

The present invention also relates to methods for skin lightening in mammals comprising topical application of the skin lightening composition of the present invention. The amount of active agent and frequency of application will vary widely depending upon the skin color already in existence in the subject, the rate of further darkening of the skin, and the level of lightening desired.

A safe and effective amount of skin lightening agent in a topical composition is applied, generally from about 1 mg to about 10 mg per $cm^2$ skin per application, preferably from about 2 mg to about 8 mg/ $cm^2$ skin per application, more preferably from about 3 mg to about 7 mg/$cm^2$ skin, also preferably from about 4 mg to about 5 mg/$cm^2$ skin. Application preferably ranges from about four times a day to about twice a week, more preferably from about three times a day to about once every other day, more preferably still from about once daily to about twice daily. Application for at least five days is required to see a skin lightening effect in lower animals. Application for at least one month is required to see an effect in humans. After lightening is achieved, the frequency and dosage can be reduced to a maintenance level, as desired. Such maintenance varies according to the individual, but is preferably from about $\frac{1}{10}$ to about $\frac{1}{2}$, more preferably from about $\frac{1}{5}$ to about $\frac{1}{3}$ of the original dosage and/or frequency, as needed.

A preferred method of the present invention for skin lightening in mammals involves applying the skin lightening composition of the present invention further comprising a safe and effective amount of one or more of a sunscreening agent, an anti-inflammatory agent, an anti-oxidant/radical scavenging agent, a chelating agent and/or a retinoid. The amount of sunscreening agent applied is preferably from about 0.01 mg to about 0.1 mg per $cm^2$ skin. The amount of anti-inflammatory agent applied is preferably from about 0.005 mg to about 0.5 mg, more preferably from about 0.01 mg to about 0.1 mg per $cm^2$ skin. The amount of anti-oxidant/radical scavenging agent preferably applied is from about 0.01 mg to about 1.0 mg, more preferably from about 0.05 mg to about 0.5 mg per $cm^2$ skin. The amount of chelating agent preferably applied is from about .001 mg to about 1.0 mg, more preferably from about 0.01 mg to about 0.5 mg, still more preferably from about 0.05 mg to about 0.1 mg per $cm^2$ skin. The amount of retinoid applied is preferably from about 0.001 mg to about 0.5 mg per $cm^2$ skin, more preferably from about 0.005 mg to about 0.1 mg per $cm^2$ skin. The amount of skin lightening agent applied is preferably from about 0.001 mg to about 2 mg per $cm^2$ skin per application, more preferably from about 0.01 mg to about 1 mg per $cm^2$ skin per application.

G. Procedure for Making a Skin Lightening Composition of the Present Invention A skin lightening composition of the present invention can be made by a conventional method. However, if a skin lightening composition of the present invention comprises the liquid crystal, the composition can be made by the steps of (i) mixing a cosmetically acceptable liquid oil, a fatty alcohol, a surfactant and lecithin at the temperature of 60° C. to 100° C. to obtain mixture 1, and (ii) mixing an water-soluble reducing agent, a polyhydric alcohol and water with the mixture 1 while maintained at the temperature of 45° C. to 100° C.

The mixture obtained by the above steps (i) and (ii) is usually cooled to room temperature.

The other component can be mixed according to the conventional manner, however, generally oil-soluble components can be added in the above step (i) and water-soluble components can be added in the above step (ii).

The liquid crystal can be detected by observing the shape of the liquid crystal by a polarization microscope.

H. EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Composition No. 1 of the present invention is shown in Table 1. Composition Nos. 2–5 of the present invention are shown in Table 2–5.

Procedure for making Composition No. 1

Caprylic/capric triglyceride (Migyol 812), cetyl alcohol, polyoxyethylene (40) monostearate and lecithin are mixed together and heated to 70° C. Then, sodium sulfite, sodium hydrogensulfite, deionized water and glycerin are added thereto with stirring and the mixture is emulsified. Then the emulsified mixture is cooled to room temperature with stirring to obtain an emulsion with a liquid crystal. The emulsion with the liquid crystal and all other ingredients than the above are mixed together to obtain Composition No. 1. The components of Composition No. 1 are shown in Table 1.

TABLE 1

Composition No. 1: Emulsion with liquid crystal

| Component | Amount (weight %) |
| --- | --- |
| Lecithin | 3.00 |
| Polyoxyethylene(40) monostearate (Myrj 52) | 1.00 |
| Cetyl Alcohol | 1.00 |
| Caprylic/Capric Triglyceride (Migyol 812) | 15.00 |
| D-delta Tocopherol | 0.10 |
| Glycerin | 5.00 |
| Propylparaben | 0.10 |
| Methylparaben | 0.20 |
| De-ionized Water | 72.13 |
| Sodium hydrogensulfite (manufactured by Nacalai tesque, INC.) | 0.08 |
| Sodium Sulfite | 0.20 |
| Sodium Hydroxide | 0.59 |
| Carboxy vinyl polymer (Carbopol 980) | 1.00 |
| Benzyl Alcohol | 0.60 |

Composition No. 1 shows a strong skin lightening activity.

TABLE 2

Composition No. 2: Clear lotion with lecithin (No liquid crystal)

| Component | Amount (weight %) |
| --- | --- |
| Denatured alcohol | 5.000 |
| Polyoxyethylene(20) sorbitan monolaurate (Tween 20) | 1.200 |
| Lecithin | 0.020 |
| De-ionized water | 87.160 |
| Sodium hydrogensulfite (manufactured by Nacalai tesque, INC.) | 0.100 |
| Sodium sulfite | 0.200 |
| 1,3-Butylene glycol | 4.000 |
| Glycerin | 2.000 |
| EDTA-2Na | 0.100 |
| Methylparaben | 0.150 |
| Citric acid anhydrous | 0.020 |
| Sodium citrate | 0.050 |

Composition No.2 can be prepared, for example, by the following method.

1. Denatured alcohol, polyoxyethylene(20) sorbitan monolaurate (Tween 20) and lecithin, are mixed and dissolved at room temperature (25° C.) to obtain mixture-1.
2. De-ionized water, sodium hydrogen sulfite, sodium sulfite, 1,3-butylene glycol, Glycerin, EDTA-2Na, methylparaben, citric acid anhydrous and sodium citrate are dissolved at room temperature (25° C.) to obtain mixture-2.
3. Mixture-1 and mixture-2 are mixed together to obtain composition No.2.

TABLE 3

Composition No. 3: Milky lotion with lecithin (No liquid crystal)

| Component | Amount (weight %) |
| --- | --- |
| Decaglyceryl monostearate | 1.200 |
| Lecithin | 0.500 |
| Cholesterol | 0.050 |
| C10–30 Cholesterol/Lanosterol Esters | 1.000 |
| Squalane | 3.000 |
| Glyceryl trioctanoate | 4.000 |
| Propylparaben | 0.050 |
| D-delta-Tocopherol | 0.050 |
| De-ionized water | 80.720 |
| Sodium hydrogensulfite (manufactured by Nacalai tesque, INC.) | 0.100 |
| Sodium sulfite | 0.300 |
| Carboxy vinyl polymer (Carbopol 941) | 0.300 |
| 1,3-Butylene glycol | 6.000 |
| Glycerin | 2.500 |
| Methylparaben | 0.100 |
| EDTA-2Na | 0.050 |
| Sodium hydroxide | 0.080 |

Composition No.3 can be prepared, for example, by the following method.

1. Decaglyceryl monostearate, lecithin, cholesterol, C10-30 cholesterol/lanosterol esters, squalane, glyceryl trioctanoate, propylparaben and D-delta-Tocopherol are mixed and dissolved at the temperature of 80° C. to obtain mixture-1.
2. De-ionized water, sodium hydrogen sulfite, sodium sulfite, carboxy vinyl polymer (Carbopol 941), 1,3-butylene glycol, Glycerin, methylparaben, EDTA-2Na and sodium hydroxide are dissolved at the temperature of 80° C. to obtain mixture-2.
3. Mixture-1 and mixture-2 are mixed together at the temperature of 80° C., then are cooled to room temperature (25° C.) to obtain composition No.3.

TABLE 4

Composition No. 4: Milky lotion with liquid crystal

| Component | Amount (weight %) |
| --- | --- |
| Polyoxyethylene (100) stearyl ether | 0.500 |
| Stearic acid | 0.550 |
| Lecithin | 0.800 |
| Cetyl alcohol | 1.300 |
| Glyceryl monohydoxy stearate | 0.750 |
| Cetyl palmitate | 3.000 |
| Petrolatum | 2.000 |
| Liquid paraffin | 2.000 |
| Octyldodecyl myristate | 0.500 |
| Methyl polysiloxane (350CS) | 0.300 |
| De-ionized water | 84.200 |
| Sodium hydrogensulfite (manufactured by Nacalai tesque, INC.) | 0.100 |
| Sodium sulfite | 0.300 |
| Carboxy vinyl polymer (Carbopol 941) | 0.050 |
| Acrylates/C10–30 alkyl acrylate crosspolymer | 0.075 |

TABLE 4-continued

Composition No. 4: Milky lotion with liquid crystal

| Component | Amount (weight %) |
| --- | --- |
| Glycerin | 3.000 |
| Methylparaben | 0.200 |
| Propylparaben | 0.150 |
| EDTA-4Na | 0.100 |
| Potassium hydroxide | 0.125 |

Composition No.4 can be prepared, for example, by the following method.
1. Polyoxyethylene (100) stearyl ether, stearic acid, lecithin, cetyl alcohol, glyceryl monohydoxy stearate, cetyl palmitate, petrolatum, liquid paraffin, octyldodecyl myristate and methyl polysiloxane (350CS) are mixed and dissolved at the temperature of 80° C. to obtain mixture-1.
2. De-ionized water, sodium hydrogen sulfite, sodium sulfite, carboxy vinyl polymer (Carbopol 941), acrylates/C10-30 alkyl acrylate crosspolymer, glycerin, methylparaben, propylparaben, EDTA-4Na and potassium hydroxide are dissolved at the temperature of 80° C. to obtain mixture-2.
3. Mixture-1 and mixture-2 are mixed together at the temperature of 80° C., then are cooled to room temperature (25° C.) to obtain composition No.4.

TABLE 5

Composition No. 5: cream with liquid crystal

| Component | Amount (weight %) |
| --- | --- |
| Stearic acid | 0.250 |
| PEG 100 stearate | 0.250 |
| Lecithin | 1.000 |
| Cetyl alcohol | 1.800 |
| Stearyl alcohol | 1.200 |
| Petrolatum | 1.500 |
| Liquid paraffin | 2.000 |
| Isopropyl palmitate | 1.000 |
| Methyl polysiloxane (350CS) | 0.500 |
| De-ionized water | 80.690 |
| Sodium hydrogensulfite (manufactured by Nacalai tesque, INC.) | 0.100 |
| Sodium sulfite | 0.300 |
| Carboxy vinyl polymer (Carbopol 934) | 0.600 |
| Glycerin | 8.000 |
| Methylparaben | 0.250 |
| Propylparaben | 0.150 |
| EDTA-2Na | 0.100 |
| Sodium hydroxide | 0.310 |

Composition No.5 can be prepared, for example, by the following method.
1. Stearic acid, PEG 100 stearate, lecithin, cethyl alcohol, stearyl alcohol, petrolatum, liquid paraffin, isopropyl palmitate and methyl polysiloxane (350CS) are mixed and dissolved at the temperature of 80° C. to obtain mixture-1.
2. De-ionized water, sodium hydrogen sulfite, sodium sulfite, carboxy vinyl polymer (Carbopol 934), Glycerin, methylparaben, propylparaben, EDTA-2Na and sodium hydroxide are dissolved at the temperature of 80° C. to obtain mixture-2.
3. Mixture-i and mixture-2 are mixed together at the temperature of 80° C., then are cooled to room temperature (25° C.) to obtain composition No.5.

The compositions of the present invention have strong skin lightening effect of mammalian skin compared versus compositions which comprise a hydroquinone derivative.

Method Example

This example sets forth a method for lightening mammalian skin using a composition of the present invention.

The composition of example No. 1 is applied 5 mg/cm$^2$ skin per application three times a day for one month. After one month, a strong skin lightening effect is seen. Once the desired level of the skin lightening is achieved, treatment is reduced to limit a day, to maintain the level of lightening.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. A skin lightening cosmetic composition consisting essentially of:
    a) from about 0.1% to about 5% by weight, of at least one water-soluble reducing agent is selected from the group consisting of sodium sulfite, potassium sulfite, ammonium sulfite, sodium hydrogen sulfite, potassium hydrogen sulfite, ammonium hydrogen sulfite, sodium metabisulfite, potassium metabisulfite, formic acid, oxalic acid, and mixtures thereof;
    b) from about 0.01% to about 10% by weight, of lecithin; and
    c) a cosmetically acceptable carrier;
        wherein the composition is substantially free of hydroquinone or its derivatives.

2. The skin lightening cosmetic composition of claim 1 wherein the water-soluble reducing agent comprises from about 0.15% to about 5% by weight, of the composition.

3. The skin lightening cosmetic composition of claim 1 wherein the water-soluble reducing agent comprises from about 0.2% to about 5% and lecithin comprises from about 0.5% to about 3% by weight, of the composition.

4. The skin lightening cosmetic composition of claim 3 wherein the water-soluble reducing agent is selected from the group consisting of sodium sulfite, sodium hydrogen sulfite, sodium metabisulfite, and mixtures thereof.

5. A skin lightening cosmetic composition consisting essentially of:
    a) from about 0.1% to about 5% by weight, of at least one water-soluble reducing agent is selected from the group consisting of sodium sulfite, potassium sulfite, ammonium sulfite, sodium hydrogen sulfite, potassium hydrogen sulfite, ammonium hydrogen sulfite, sodium metabisulfite, potassium metabisulfite, formic acid, oxalic acid, and mixtures thereof;
    b) from about 0.01% to about 10% by weight, of lecithin;
    c) from about 1% to about 50% by weight, of a cosmetically acceptable liquid oil;
    d) from about 0.1% to about 20% by weight, of a polyhydric alcohol;
    e) from about 0.1% to about 20% by weight, of a solid fatty alcohol;
    f) from about 0.1% to about 10% by weight, of a surfactant;
    g) from about 40% to about 90% by weight, of water;
        wherein the composition is substantially free of hydroquinone or its derivatives, and at least a portion of the above components (a), (b), (c), (d), (e), (f), and (g) forms a liquid crystal.

6. The skin lightening cosmetic composition of claim 5, wherein:
   a) the water-soluble reducing agent comprises from about 0.15% to about 5%;
   b) lecithin comprises from about 0.1% to about 3%;
   c) the cosmetically acceptable liquid oil comprises from about 3% to about 25%;
   d) the polyhydric alcohol comprises from about 1% to about 10%;
   e) the solid fatty alcohol comprises from about 1.0% to about 5%;
   f) the surfactant comprises from about 0.1% to about 3%; and
   g) the water comprises from about 60% to about 90% by weight, of the composition.

7. The skin lightening cosmetic composition of claim 6 wherein said reducing agent is selected from the group consisting of sodium sulfite, sodium hydrogen sulfite, sodium metabisulfite and mixtures thereof.

8. The skin lightening cosmetic composition of claim 6 wherein the cosmetically acceptable liquid oil is a triglyceride.

9. The skin lightening cosmetic composition of claim 6 wherein the cosmetically acceptable liquid oil is caprylic/capric triglyceride.

10. The skin lightening cosmetic composition of claim 6 wherein the polyhydric alcohol is glycerin.

11. The skin lightening cosmetic composition of claim 6 wherein the solid fatty alcohol is cetyl alcohol.

12. The skin lightening cosmetic composition of claim 6 wherein the composition is an emulsion.

13. A method for skin lightening comprising topically applying the cosmetic composition of claim 1 to the skin of a person in need of skin lightening.

14. A method for skin lightening comprising topically applying the cosmetic composition of claim 5 to the skin of a person in need of skin lightening.

15. A process for preparing a skin lightening cosmetic composition comprising the steps of:
   i) mixing
      a) a cosmetically acceptable liquid oil;
      b) a solid fatty alcohol;
      c) a surfactant; and
      d) lecithin;
         at the temperature of 60° C. to 100° C. to obtain mixture 1; and
   ii) mixing with the mixture 1
      e) a water-soluble reducing agent;
      f) a polyhydric alcohol; and
      g) water;
         at the temperature of 45° C. to 100° C.;
         wherein the composition is substantially free of hydroquinone or its derivatives, and at least a portion of the above components (a), (b), (c), (d), (e), (f), and (g) forms a. liquid crystal.

16. The process for preparing a skin lightening cosmetic composition according to claim 15 wherein:
   a) the cosmetically acceptable liquid oil comprises from about 1% to about 50%;
   b) the solid fatty alcohol comprises from about 0.1% to about 20%;
   c) the surfactant comprises from about 0.1% to about 10%;
   d) the lecithin comprises from about 0.01% to about 10;
   e) the water-soluble reducing agent comprises from about 0.1% to about 5%;
   f) the polyhydric alcohol comprises from about 0.1% to about 20%; and
   g) the water comprises from about 40% to about 90% by weight, of the composition.

17. The process for preparing a skin lightening cosmetic composition according to claim 16 wherein the water-soluble reducing agent is selected from the group consisting of sodium sulfite, potassium sulfite, ammonium sulfite, sodium hydrogen sulfite, potassium hydrogen sulfite, ammonium hydrogen sulfite, sodium metabisulfite, potassium metabisulfite, formic acid, oxalic acid, and mixtures thereof.

* * * * *